US008873711B2

(12) United States Patent
Engelbart et al.

(10) Patent No.: US 8,873,711 B2
(45) Date of Patent: Oct. 28, 2014

(54) METHOD AND SYSTEM FOR VISUALIZING EFFECTS OF CORROSION

(75) Inventors: Roger W. Engelbart, St. Louis, MO (US); Taisia V. Tsukruk, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/527,068

(22) Filed: Jun. 19, 2012

(65) Prior Publication Data
US 2013/0336455 A1    Dec. 19, 2013

(51) Int. Cl.
    *G01N 23/203* (2006.01)
(52) U.S. Cl.
    USPC .................................... 378/87; 378/86
(58) Field of Classification Search
    CPC .................................... G01N 23/203
    USPC ............................... 378/87, 88
    See application file for complete search history.

(56) References Cited

U.S. PATENT DOCUMENTS

| | | | | |
|---|---|---|---|---|
| 6,000,844 | A * | 12/1999 | Cramer et al. | 374/5 |
| 7,508,910 | B2 | 3/2009 | Safai et al. | |
| 7,623,626 | B2 | 11/2009 | Safai et al. | |
| 7,649,976 | B2 | 1/2010 | Georgeson et al. | |
| 8,138,471 | B1 * | 3/2012 | Shedlock et al. | 250/269.1 |
| 2004/0156737 | A1 * | 8/2004 | Rakowski | 420/53 |
| 2005/0151841 | A1 * | 7/2005 | Nelson et al. | 348/82 |
| 2006/0058974 | A1 * | 3/2006 | Lasiuk et al. | 702/97 |
| 2007/0222436 | A1 * | 9/2007 | Gao et al. | 324/220 |
| 2008/0307886 | A1 * | 12/2008 | Marsh et al. | 73/601 |
| 2009/0234590 | A1 * | 9/2009 | McNealy et al. | 702/38 |
| 2012/0240819 | A1 * | 9/2012 | Hartley et al. | 106/13 |

OTHER PUBLICATIONS

Nucsafe—Backscatter Radiography, including two downloaded documents dated 2012; [online] [retrieved Jul. 17, 2012]. Retrieved from the Internet: <URL: http://www.nucsafe.com/cms/Backscatter+Radiography/79.html>. 6 pages.

* cited by examiner

*Primary Examiner* — Hoon Song
*Assistant Examiner* — Danielle Fox
(74) *Attorney, Agent, or Firm* — Alston & Bird LLP

(57) ABSTRACT

A method and system for visualizing the effects of corrosion are provided. In the context of a method, a workpiece is interrogated with radiation, such as by interrogating the workpiece with x-ray radiation. By relying upon a radiographic technique, the workpiece may be hidden and may be interrogated without disassembly. The method generates a backscatter image of the workpiece based upon radiation backscattered from the workpiece. The method also compares one or more regions of the backscatter image of the workpiece with respect to backscatter images of different metal loss indicators. Each metal loss indicator is representative of a different amount of metal loss. As a result of the comparison, the method estimates the metal loss attributable to corrosion of the workpiece.

19 Claims, 5 Drawing Sheets

METHOD AND SYSTEM FOR VISUALIZING EFFECTS OF CORROSION

TECHNOLOGICAL FIELD

An example embodiment of the present disclosure relates generally to a method and system for detecting corrosion and, more particularly, to a method and system for visualizing the effects of corrosion.

BACKGROUND

It is oftentimes desirable to inspect a workpiece in order to detect anomalies, such as the effects of corrosion. For example, vehicles, such as aircraft, trains, automobiles and other motor vehicles, and other structures may include a number of structural components that are desirably inspected in order to identify anomalies, such as the effects of corrosion. Although some of the structural components are readily accessible so as to be inspected visually, a number of the structural components, such as the stringers of an aircraft, are positioned in a remote location so as to be hidden from view or to otherwise be of limited access.

In order to inspect these hidden structural components, a structural assembly may be disassembled and, following inspection, may then be reassembled, thereby resulting in substantial expense and downtime. With respect to an aircraft, for example, the disassembly, inspection and subsequent reassembly may require a number of man hours and lead to significant aircraft downtime at a repair depot. In order to avoid disassembly of a structural assembly, non-destructive inspection techniques have been developed, such as radiography, ultrasonic and eddy current inspection techniques. The type of non-destructive inspection technology that is utilized may be dependent upon the type of anomaly to be detected, the type of material to be inspected, the location at which the inspection will occur and the complexity of the structural assembly in and around the location that will be inspected.

Some remote locations of a structural assembly may be prone to corrosion as a result of the intrusion and retention of moisture. Since the need for corrective action, if any, is dependent upon the severity of the corrosion which may, in turn, be measured by the percent of the total thickness of the structure that has been lost due to corrosive activity, radiography may provide a non-destructive inspection technique to facilitate the inspection of such remote locations without disassembly in order to determine the effects of corrosion. In order to non-destructively inspect a structural component using radiography, an x-ray source may be placed on one side of the structural component and an imaging medium may be placed on the other side of the structural component. As such, while the structural assembly need not necessarily be disassembled, access is generally required to both sides, that is, the opposite sides of the structural component to be inspected. While access to the opposite sides of a structural component to be inspected is available in some instances, the opposite sides of some structural components may not be readily accessed and, as such conventional radiographic techniques may be unavailable for non-destructive inspection purposes.

BRIEF SUMMARY

A method and system for visualizing the effects of corrosion are provided in accordance with an example embodiment of the present disclosure. In this regard, the method and system of one embodiment rely upon backscattered radiation such that access is only required to one side of the workpiece that is to be inspected. As such, a workpiece may be inspected in a non-destructive manner without disassembly or, at least, without significant disassembly, while requiring access to only one side of the workpiece. By relying upon backscattered radiation, such as backscattered x-rays, the method and system of one embodiment may detect and permit visualization of corrosion, even if the workpiece is hidden from view, thereby permitting evaluation and, if necessary, repair of the workpiece in an orderly manner.

In one embodiment, a method is provided for visualizing the effects of corrosion that includes interrogating a workpiece with radiation, such as by interrogating the workpiece with x-ray radiation. By relying upon a radiographic technique, the workpiece may be hidden and may be interrogated without disassembly. The method of this embodiment also generates a backscatter image of the workpiece based upon radiation backscattered from the workpiece. The method also compares one or more regions of the backscatter image of the workpiece with respect to backscatter images of different metal loss indicators. Each metal loss indicator is representative of a different amount of metal loss. As a result of the comparison, the method of this embodiment also estimates the metal loss attributable to corrosion of the workpiece.

Each metal loss indicator may be representative of a different percentage of metal loss. In this regard, the plurality of metal loss indicators of one embodiment may be representative of respective percentages of metal loss that are more closely spaced for smaller percentages than for larger percentages. The method of one embodiment may also include generating the backscatter images of the different metal loss indicators which, in turn, are compared to one or more regions of the backscatter image of the workpiece. In regards to comparing one or more regions of the backscatter image of the workpiece with respect to backscatter images of the different metal loss indicators, the method may compare grayscale levels of the one or more regions of the backscatter image of the workpiece with grayscale levels of the respective backscatter images of the different metal loss indicators.

In another embodiment, a system for visualizing the effects of corrosion is provided that includes a backscatter imaging system configured to interrogate a workpiece with radiation, such as x-ray radiation, and to generate a backscatter image of the workpiece based upon radiation backscattered from the workpiece. As such, the backscatter imaging system of one embodiment may permit inspection of a workpiece that is hidden and may allow interrogation without disassembly. In this embodiment, the backscatter imaging system may also be configured to generate respective backscatter images of different metal loss indicators with each metal loss indicator representative of a different amount of metal loss. As such, one or more regions of the backscatter image of the workpiece may be compared with the respective backscatter images of the different metal loss indicators for which the metal loss attributable to corrosion of the workpiece is estimatable.

Each metal loss indicator may be representative of a different percentage of metal loss. In this regard, the plurality of metal loss indicators of one embodiment may be representative of respective percentages of metal loss that are more closely spaced for smaller percentages than for larger percentages. In one embodiment, the backscatter imaging system is configured to generate the backscatter image of the workpiece and the backscatter images of the different metal loss indicators to permit a comparison of grayscale levels of the one or more regions of the backscatter image of the workpiece with grayscale levels of the respective backscatter images of different metal loss indicators.

In a further embodiment, a system for visualizing effects of corrosion is provided that includes a backscatter imaging system and a plurality of metal loss indicators. In this embodiment, the backscatter imaging system is configured to interrogate a workpiece with radiation and to generate a backscatter image of the workpiece based upon radiation backscattered from the workpiece. Each metal loss indicator is representative of a different amount of metal loss. The backscatter imaging system of this embodiment is also configured to generate respective backscatter images of different metal loss indicators to permit a comparison of one or more regions of the backscatter image of the workpiece with respective backscatter images of the different metal loss indicators for which the metal loss attributable to corrosion of the workpiece is estimable. As such, the system of this embodiment may permit the inspection of a workpiece that is hidden and may allow interrogation without disassembly.

In one embodiment, each metal loss indicator is representative of a different percentage of metal loss. In this regard, the plurality of metal loss indicators may be representative of respective percentages of metal loss that are more closely spaced for smaller percentages than for larger percentages. The backscatter imaging system of one embodiment may be configured to generate the backscatter image of the workpiece and the backscatter images of different metal loss indicators to permit a comparison of grayscale levels of the one or more regions of the backscatter image of the workpiece with grayscale levels of the respective backscatter images of different metal loss indicators.

BRIEF DESCRIPTION OF THE DRAWINGS

Figure 1:
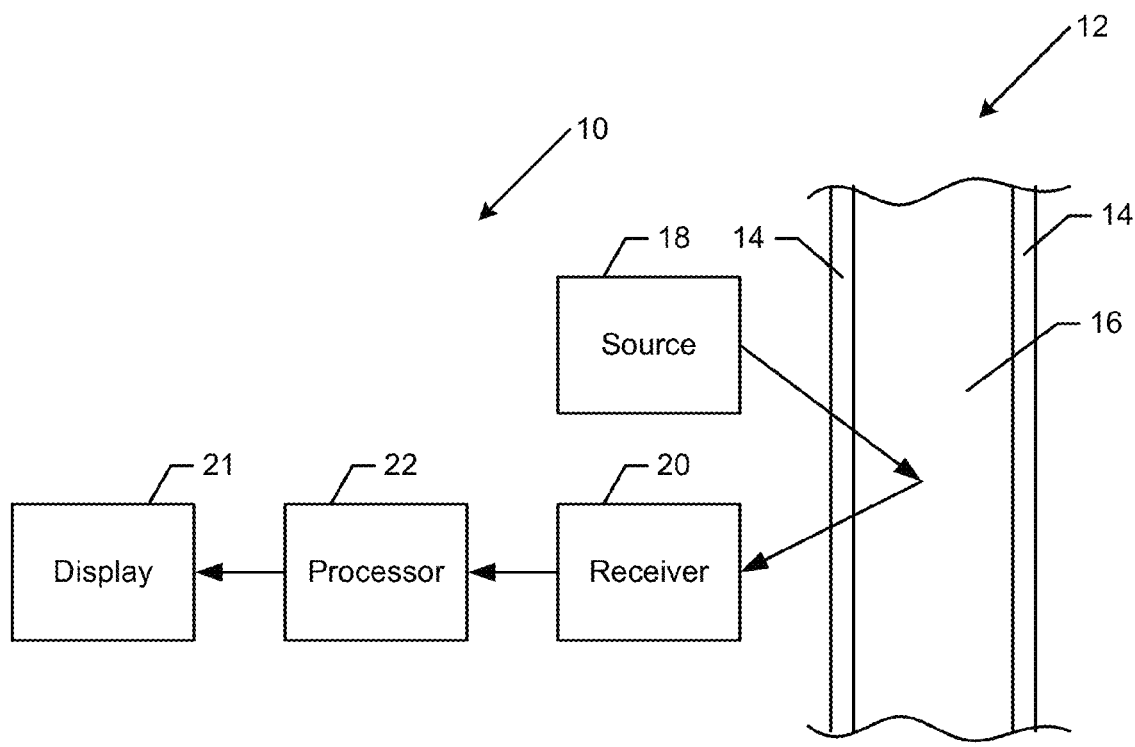
Figure 2:
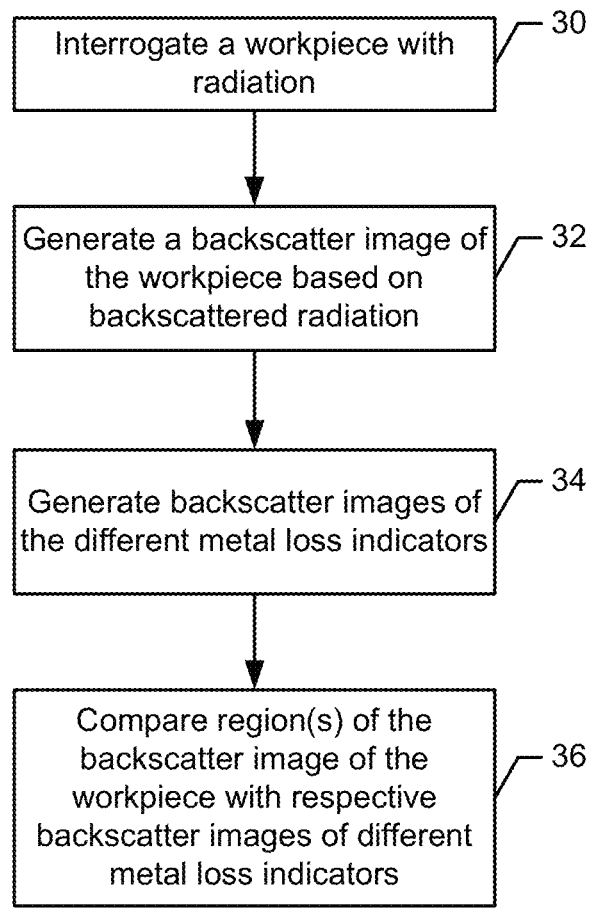
Figure 3:
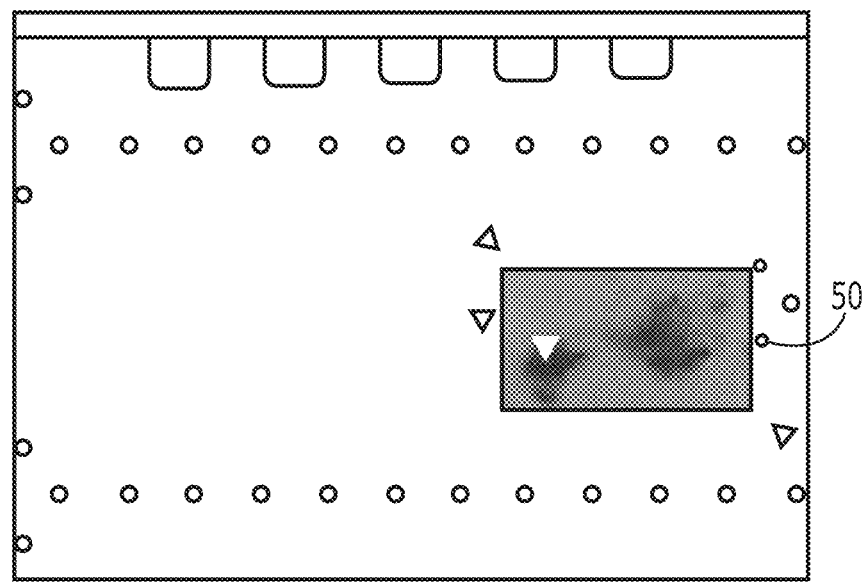
Figure 4:
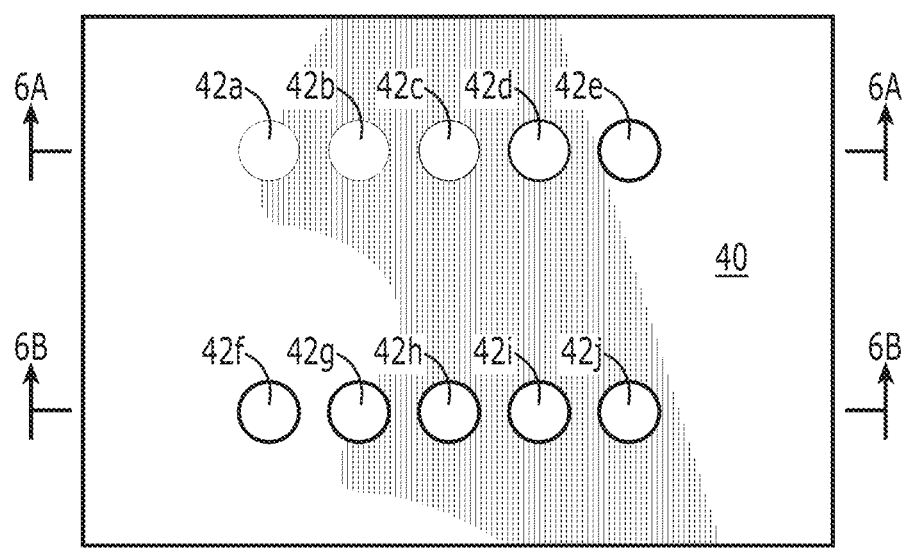
Figure 5:
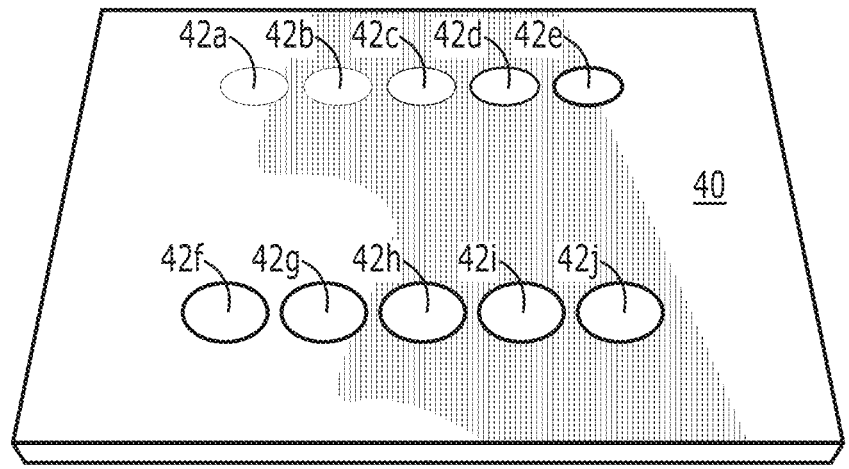
Figure 6A:
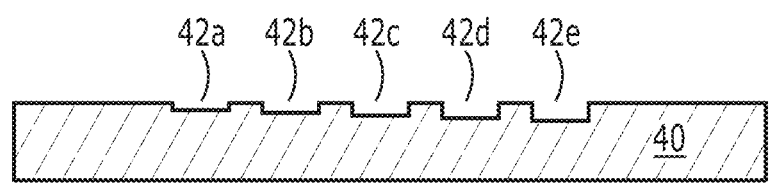
Figure 6B:
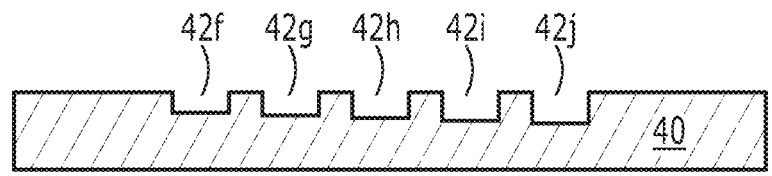
Figure 7:
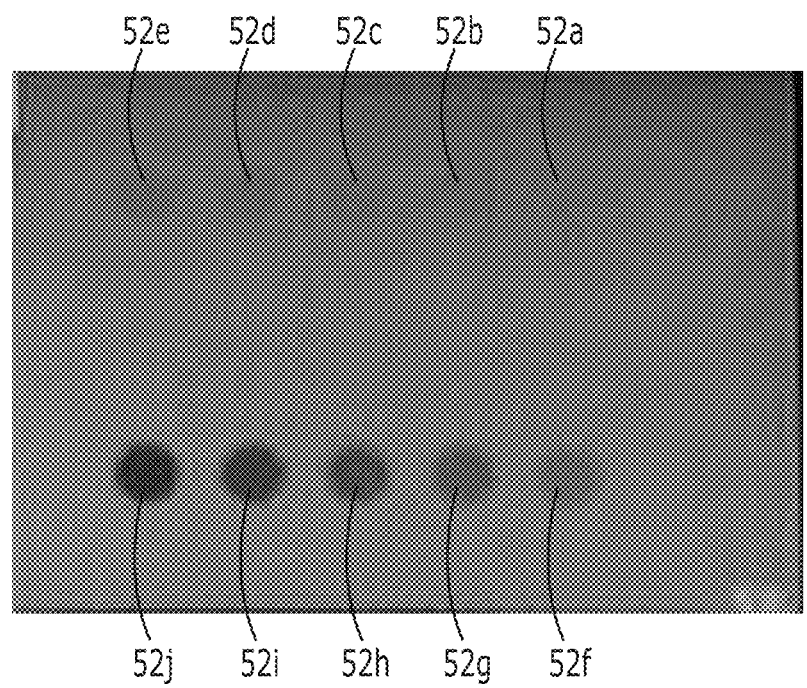

Having thus described example embodiments of the present disclosure in general terms, reference will now be made to the accompanying drawings, which are not necessarily drawn to scale, and wherein:

FIG. 1 is a schematic representation of a system in accordance with one example embodiment of the present disclosure;

FIG. 2 is a flow chart of the operations performed in accordance with an example embodiment of the present disclosure;

FIG. 3 is an example of a backscatter image of a workpiece that includes one or more regions that may be indicative of corrosion that is generated in accordance with an example embodiment of the present disclosure;

FIG. 4 is a plan view of a plurality of metal loss indicators in accordance with an example embodiment of the present disclosure;

FIG. 5 is a perspective view of the plurality of metal loss indicators of FIG. 4;

FIGS. 6A and 6B are cross-sectional views of the plurality of metal loss indicators taken along lines 6A-6A and 6B-6B, respectively, of FIG. 4; and FIG. 7 is the backscatter images of different metal loss indicators that are generated in accordance with an example embodiment of the present disclosure.

DETAILED DESCRIPTION

The present disclosure now will be described more fully with reference to the accompanying drawings, in which some, but not all embodiments of the invention are shown. This disclosure may be embodied in many different forms and should not be construed as limited to the embodiments set forth; rather, these embodiments are provided so that this disclosure will be thorough and complete, and will fully convey the scope of the invention to those skilled in the art. Like numbers refer to like elements throughout.

Referring now to FIG. 1, a system 10 for visualizing the effects of corrosion upon a workpiece 16 is illustrated. The system 10 may provide for the inspection of a variety of workpieces 16. In this regard, the workpiece 16 may be a structural component of a wide variety of different structural assemblies 12 including, for example, vehicles, such as aircraft, trains, automobiles and other motor vehicles. However, the workpiece 16 that is inspected may be a structural component of other types of structural assemblies 12, such as a building, a bridge or the like. Additionally, the workpiece 16 may be formed of various materials, but in one embodiment, is formed of metal.

While the method and system of an example embodiment may inspect workpieces 16 that are visible or otherwise easily accessible and while the system and method of an example embodiment may inspect workpieces following disassembly of the structural assembly 12 of which the workpiece is a structural component, the system and method of one embodiment is configured to inspect workpieces that are hidden in a manner that permits the workpiece to be interrogated or inspected without disassembly. In this regard, the workpiece 16 may be positioned within an interior portion of a structural assembly 12 that has limited or remote access. For example, the workpiece 16 that is inspected may be disposed within a structural assembly 12 in a manner that the workpiece is unable to be viewed without disassembly of at least a portion of the structural assembly. With respect to an aircraft, a number of structural components, such as stringers, are disposed within the aircraft in such a manner as not to be visible without disassembly of other portions of the aircraft. By way of example, but not of limitation, FIG. 1 illustrates a workpiece 16 that is sandwiched between and hidden from view by first and second outer structural members 14. As shown, the workpiece 16 of this example is not visible without removal of one or both of the outer structural members 14 and, as such, is hidden from site without disassembly. However, workpieces 16 that are hidden may sometimes be subject to corrosion as a result of the intrusion and retention of moisture in a manner that is not visible without disassembly of the structural assembly 12. As such, the method and system of an example embodiment permit the effects of corrosion upon the workpiece 16, such as a workpiece hidden from sight, to be detected and visualized, thereby allowing decisions to be made with respect to any repairs and, if so, the timing of such repairs to be made in an orderly manner that does not disrupt or that at least limits the disruption in the schedule of the structural assembly 12.

The system 10 of FIG. 1 includes a source 18 of radiation. While various types of radiation may be employed, the source 18 of one embodiment is an x-ray source permitting x-rays to be generated. In this embodiment, the x-ray source 18 may have various power levels depending upon the thickness and radiation absorption characteristics of the workpiece 16 and the thickness and radiation absorption characteristics of the other structural components surrounding the workpiece. In one embodiment, however, the x-ray source 18 is a 160 kv x-ray tube, while in another embodiment, the x-ray source is a 220 kv x-ray tube. Indeed, depending upon the workpiece 16 to be inspected and the structural assembly 12 of which the workpiece is a component, the exposure requirements, such as the kilovoltage, milliamperage, scan speed and stand-off distance, may be modified.

As shown in block 30 of FIG. 2, the source 18 is configured to interrogate the workpiece 16 with radiation, such as by interrogating the workpiece with x-ray radiation. While the workpiece 16 may be interrogated in various manners, the source 18 of one embodiment is configured to generate a relatively small beam of radiation, such as a pencil-sized beam of radiation, that is scanned, such as by being raster scanned, across the workpiece or at least a portion of the workpiece.

The impingement of the radiation, such as the x-rays, upon the workpiece 16 causes photons to be backscattered. As such, the system 10 of FIG. 1 includes a receiver 20, such as a photon detector, for capturing the photons scattered by the workpiece 16 as a result of the impingement of the radiation thereon. Based upon the radiation backscattered from the workpiece 16, such as the scattered photons captured by the receiver 20, such as the photon detector, the system 10 generates a backscatter image of the workpiece 16 as shown in block 32 of FIG. 2. The scattered photons generated by the impingement of the radiation upon the workpiece 16 that are detected by the receiver 20, such as a photon detector, may, in one embodiment, be processed, such as by a processor 22, e.g., a video processor or other computing device, so as to generate a backscatter image of the workpiece based upon radiation backscattered from the workpiece. The backscatter image that is generated may be presented upon a display 24 that is driven by the receiver 20 and, in turn, by the processor 22. Although various types of backscatter images may be generated, one example of a backscatter image is shown in FIG. 3. While the backscatter images may be presented in color, the backscatter images of one embodiment are black and white images with the effects of corrosion generally indicated by a darker region 50 of the image that is representative of thinner portions of the workpiece 16, such as portions of the workpiece that have been thinned as a result of the loss of material due to corrosive effects. In this regard, the example image of FIG. 3 includes a region 50 that may have been subjected to corrosion as a result of the darker areas within the region.

By relying upon backscattered photons in order to generate the image of the workpiece 16, both the source 18 of the radiation and the receiver 20, processor 22 and display 24 may be positioned upon the same side of the workpiece. As such, the method and system of this embodiment not only permits a workpiece 16 to be interrogated in an instance in which the workpiece is hidden and without requiring disassembly of the structural assembly 12 that includes the workpiece, but permits the non-destructive inspection to be performed from a single side of the workpiece, thereby avoiding any need for access to the opposite sides of the workpiece. As a result, the method and system of an example embodiment are able to inspect a greater number of workpieces 16 since the method and system of an example embodiment are able to inspect workpieces that cannot be accessed from both sides.

As shown in block 36 of FIG. 2, one or more regions 50 of the backscatter image of the workpiece 16 may be compared with respective backscatter images of different metal loss indicators. In this regard, each metal loss indicator may be representative of a different amount, such as a different percentage, of metal loss. This comparison may be performed manually, such as by an inspector or other technician who visually compares one or more regions 50 of the backscatter image of the workpiece 16 with respect to backscatter images of different metal loss indicators. Alternatively, this comparison may be formed in an automated manner, such as by the processor 22.

Although the metal loss indicators 42 may be discrete and individualized indicators, a plurality of metal loss indicators of one example are shown in FIGS. 4 and 5. In this regard, a metal loss indicator panel 40 includes a plurality of metal loss indicators 42. The metal loss indicator panel has a predefined thickness, such as 0.375 inches in one example embodiment, and is formed of a material, such as a metal, e.g., aluminum, that may be interrogated by radiation, e.g., x-rays. In one embodiment, the metal loss indicator panel is formed of a material having the same radiation absorption characteristics as the workpiece, such as by being formed of the same material as the workpiece. The metal loss indicator panel may also have the same thickness of the workpiece, but may have a different thickness than the workpiece. Each metal loss indicator 42 of the metal loss indicator panel 40 is a region of the metal loss indicator panel from which a different thickness of material has been removed. In one embodiment, for example, each metal loss indicator 42 may be representative of a different percentage of metal loss. See FIGS. 6A and 6B. Indeed, in one embodiment, the plurality of metal loss indicators 42 representative of respective percentages of metal loss are more closely spaced for smaller percentages than for larger percentages in order to facilitate the resolution with which metal loss attributable to corrosion may be detected by the system and method of an example embodiment. Although the metal loss indicators 42 may be representative of different amounts, such as different percentages, of metal loss, the metal loss indicators 42a, 42b, 42c, 42d, 42e, 42f, 42g, 42h, 42i and 42j of one embodiment may be representative of the removal of one percent, two percent, three percent, four percent, five percent, ten percent, fifteen percent, twenty percent, and thirty percent, respectively, of the thickness of the metal loss indicator panel 40. In one embodiment, the metal loss indicator panel has a different thickness than the workpiece, but the metal loss indicators advantageously represent different percentages of metal loss relative to the thickness of the workpiece.

In the illustrated embodiment, the plurality of metal loss indicators 42 are formed by removing material from a metal loss indicator panel 40 that is otherwise of a uniform thickness. However, the metal loss indicators 42 need not be formed by the removal of material, but, instead, the metal loss indicators may be initially formed so as to define regions that are thinner than other regions of the metal loss indicator panel 40. Additionally, while a metal loss indicator panel 40 including a plurality of metal loss indicators 42 is shown in FIGS. 4 and 5 and will be described herein by way of example, the plurality of metal loss indicators need not be carried by a single metal loss indicator panel, but may instead be separated from one another.

The backscatter images of the metal loss indicators 42 may be generated as shown in block 34 of FIG. 2 by irradiating the metal loss indicators, such as with x-rays. In one embodiment, either same or a different source of radiation may irradiate the metal loss indicators, such as by scanning a beam of radiation across the metal loss indicators 42 and then capturing the photons that are scattered, such as with a receiver, e.g., a photon detector. Based upon the captured photons, backscatter images of the metal loss indicators 42 may be generated, such as by a processor, and displayed, such as upon a display. See, for example, FIG. 7.

As indicated above, one or more regions 50 of the backscatter image of the workpiece 16 may be compared with respective backscatter images of different metal loss indicators 42. The backscatter images of different metal loss indicators 42 of one embodiment, such as the backscatter images of the metal loss indicators of the metal loss indicator panel 40 of FIGS. 4 and 5, are shown in FIG. 7. As described above in conjunction with the backscatter image of the workpiece 16, the backscatter images of the metal loss indicators 42 may be presented in various manners including with various colors, but, in one embodiment, are presented in black and white with various grayscale levels being indicative of the thickness of the material. In this regard, thinner regions of material may be indicated by darker regions of the image with the darkness of the image varying directly, such as proportionately, with the thinness of the materials. As such, in this embodiment, those regions of the material being inspected that are thinner create darker regions of the backscatter image, while those regions of the material being inspected that are thicker create lighter regions of the backscatter image. As referenced herein, the comparison of the backscatter images also includes a determination as to which, if any, of the backscatter images of the different metal loss indicators 42 match the one or more regions of the backscatter image of the workpiece 16. In this regard, a backscatter image of a metal loss indicators 42 may be considered to match one or more regions of the backscatter image of the workpiece 16 in an instance in which the color or the gray scale levels of the backscatter image is identical or are within a predefined range of one another.

The backscatter images of the different metal loss indicators that are shown in FIG. 7 include backscatter images 52a, 52b, 52c, 52d, 52e, 52f, 52g, 52h, 52i and 52j that correspond to the backscatter images generated by interrogation of metal loss indicator 42a, 42b, 42c, 42d, 42e, 42f, 42g, 42h, 42i and 42j, respectively. As will be apparent, the grayscale levels of the backscatter images 52 associated with the different metal loss indicators 42 become progressively darker as the images progress from the image generated by the metal loss indicator representative of the thickest sample from which the least material has been lost, that is, metal loss indicator 42a and corresponding backscatter image 52a, to the backscatter image of the metal loss indicator that is representative of the thinnest sample from which the most material has been lost, that is, metal loss indicator 42j and corresponding backscatter image 52j.

By comparing the backscatter images 52 of the different metal loss indicators 42 to the regions 50 of the backscatter image of the workpiece 16 that may be indicative of the effects of corrosion, such as the darker regions of the backscatter image of the workpiece that may be representative of the thinning of the workpiece due to corrosion, the material loss attributable to corrosion in the workpiece may be identified and, in some instances, estimated. In this regard, the metal loss attributable to corrosion of the workpiece 16 may be estimated by an inspector or other technician based upon a visual comparison or may be performed in an automated manner, such as by the processor 22. In one embodiment in which the backscatter images of the workpiece and the different metal loss indicators are presented in black and white, such as shown in FIGS. 3 and 7, the comparison may be performed by comparing the grayscale levels of the one or more regions 50 of the backscatter image of the workpiece 16 with grayscale levels of the respective backscatter images 52 of different metal loss indicators 42.

Once the metal loss attributable to corrosion is identified and, in some instances, estimated, a determination may be made as to whether the workpiece 16 requires repair and, if so, if the repair should be performed immediately or at some later time. If a repair may be made at a later time, the repair may be scheduled at a more convenient time, such as in an instance in which the structural assembly of which the workpiece 16 is a component is otherwise going to be subjected to inspection and repair. For example, in an instance in which the workpiece 16 is a structural component of an aircraft, the repair may be scheduled for the next time that the aircraft is going to visit the repair depot for routine maintenance, thereby avoiding the adverse impacts of having to take the aircraft out of service unexpectedly.

Many modifications and other embodiments set forth herein will come to mind to one skilled in the art to which these embodiments pertain having the benefit of the teachings presented in the foregoing descriptions and the associated drawings. Therefore, it is to be understood that the embodiments are not to be limited to the specific ones disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/ or functions other than those explicitly described above are also contemplated as may be set forth in some of the appended claims. Although specific terms are employed herein, they are used in a generic and descriptive sense only and not for purposes of limitation.

That which is claimed:

1. A method for visualizing effects of corrosion, the method comprising:
    interrogating a workpiece with radiation;
    generating a backscatter image of the workpiece based upon radiation backscattered from the workpiece;
    comparing, with a processor, one or more regions of the backscatter image of the workpiece with each of a plurality of backscatter images of different respective metal loss indicators, each metal loss indicator being a physical representation of a different amount of metal loss, wherein comparing comprises determining which of the plurality of backscatter images of the different respective metal loss indicators match the one or more regions of the backscatter image of the workpiece by having colors or gray scale levels that are identical or within a predefined range of one another; and
    as a result of the comparing, estimating, with the processor, the metal loss attributable to corrosion of the workpiece.

2. A method according to claim 1, wherein each metal loss indicator is representative of a different percentage of metal loss.

3. A method according to claim 2, wherein the plurality of metal loss indicators are representative of respective percentages of metal loss with the respective percentages being more closely spaced for smaller percentages than for larger percentages.

4. A method according to claim 1, wherein comparing one or more regions of the backscatter image of the workpiece with each of the plurality of backscatter images of different respective metal loss indicators comprises comparing grey scale levels of the one or more regions of the backscatter image of the workpiece with grey scale levels of the respective backscatter images of different metal loss indicators.

5. A method according to claim 1, wherein interrogating a workpiece with radiation comprises interrogating the workpiece with x-ray radiation.

6. A method according to claim 1, further comprising generating the backscatter images of the different metal loss indicators.

7. A method according to claim 1, wherein the workpiece is hidden and is interrogated without disassembly.

8. A system for visualizing effects of corrosion, the system comprising:

a backscatter imaging system configured to interrogate a workpiece with radiation and to generate a backscatter image of the workpiece based upon radiation backscattered from the workpiece, wherein the backscatter imaging system is also configured to generate respective backscatter images of different metal loss indicators with each metal loss indicator being a physical representation of a different amount of metal loss to permit a comparison of one or more regions of the backscatter image of the workpiece with each of a plurality of backscatter images of the different respective metal loss indicators for which the metal loss attributable to corrosion of the workpiece is estimable, and wherein the backscatter imaging system comprises a processor and is further configured to determine which of the plurality of backscatter images of the different respective metal loss indicators match the one or more regions of the backscatter image of the workpiece by having colors or gray scale levels that are identical or within a predefined range of one another.

9. A system according to claim 8, wherein each metal loss indicator is representative of a different percentage of metal loss.

10. A system according to claim 9, wherein the plurality of metal loss indicators are representative of respective percentages of metal loss with the respective percentages being more closely spaced for smaller percentages than for larger percentages.

11. A system according to claim 8, wherein the backscatter imaging system is configured to generate the backscatter image of the workpiece and the backscatter images of different metal loss indicators to permit a comparison of grey scale levels of the one or more regions of the backscatter image of the workpiece with grey scale levels of the respective backscatter images of different metal loss indicators.

12. A system according to claim 8, wherein the backscatter imaging system comprises an x-ray source configured to interrogate the workpiece with x-ray radiation.

13. A system according to claim 8, wherein the workpiece is hidden and is interrogated without disassembly.

14. A system for visualizing effects of corrosion, the system comprising:

a backscatter imaging system configured to interrogate a workpiece with radiation and to generate a backscatter image of the workpiece based upon radiation backscattered from the workpiece; and a plurality of metal loss indicators, each metal loss indicator being a physical representation of a different amount of metal loss, wherein the backscatter imaging system is also configured to generate respective backscatter images of different metal loss indicators to permit a comparison of one or more regions of the backscatter image of the workpiece with each of a plurality of backscatter images of the different respective metal loss indicators for which the metal loss attributable to corrosion of the workpiece is estimable, and wherein the backscatter imaging system comprises a processor and is further configured to determine which of the plurality of backscatter images of the different respective metal loss indicators match the one or more regions of the backscatter image of the workpiece by having colors or gray scale levels that are identical or within a predefined range of one another.

15. A system according to claim 14, wherein each metal loss indicator is representative of a different percentage of metal loss.

16. A system according to claim 15, wherein the plurality of metal loss indicators are representative of respective percentages of metal loss with the respective percentages being more closely spaced for smaller percentages than for larger percentages.

17. A system according to claim 14, wherein the backscatter imaging system is configured to generate the backscatter image of the workpiece and the backscatter images of different metal loss indicators to permit a comparison of grey scale levels of the one or more regions of the backscatter image of the workpiece with grey scale levels of the respective backscatter images of different metal loss indicators.

18. A system according to claim 14, wherein the backscatter imaging system comprises an x-ray source configured to interrogate the workpiece with x-ray radiation.

19. A system according to claim 14, wherein the workpiece is hidden and is interrogated without disassembly.

* * * * *